United States Patent
Mitelberg et al.

(10) Patent No.: US 6,612,012 B2
(45) Date of Patent: Sep. 2, 2003

(54) METHOD OF MANUFACTURING SMALL PROFILE MEDICAL DEVICES

(75) Inventors: Vladimir Mitelberg, Aventura, FL (US); Dieter Stoeckel, Los Altos, CA (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 8 days.

(21) Appl. No.: 09/878,529

(22) Filed: Jun. 11, 2001

(65) Prior Publication Data

US 2002/0184750 A1 Dec. 12, 2002

(51) Int. Cl.[7] .............................. B23P 11/02; A61F 2/06
(52) U.S. Cl. ................... 29/447; 29/557; 219/121.67; 148/426; 623/1.18; 623/1.19
(58) Field of Search .................... 29/447, 452, 557; 219/121.6, 121.67, 121.68, 121.69, 121.73, 121.72; 148/426, 675; 623/1.15, 1.18, 1.19

(56) References Cited

U.S. PATENT DOCUMENTS

| | | | |
|---|---|---|---|
| 3,123,072 A | * | 3/1964 | Bellamy, Jr. .................. 29/447 |
| 5,092,941 A | * | 3/1992 | Miura ........................ 148/426 |
| 5,108,407 A | * | 4/1992 | Geremia et al. ............ 606/108 |
| 5,122,136 A | * | 6/1992 | Guglielmi et al. ............. 606/32 |
| 5,852,277 A | * | 12/1998 | Gustafson ............... 219/121.67 |
| 5,911,752 A | | 6/1999 | Dustrude et al. |
| 6,042,606 A | * | 3/2000 | Frantzen ..................... 623/1.18 |
| 6,106,642 A | * | 8/2000 | DiCarlo et al. ............. 148/675 |
| 6,114,653 A | * | 9/2000 | Gustafson ............... 219/121.72 |
| 6,131,266 A | * | 10/2000 | Saunders ...................... 29/557 |
| 6,160,240 A | * | 12/2000 | Momma et al. .......... 219/121.6 |
| 6,253,443 B1 | * | 7/2001 | Johnson ........................ 29/557 |

FOREIGN PATENT DOCUMENTS

| | | |
|---|---|---|
| DE | 197 45 294 A1 | 4/1999 |
| DE | 198 31 721 A1 | 1/2000 |
| DE | 199 52 295 A1 | 5/2001 |
| WO | WO 98/51238 | 11/1998 |
| WO | WO 00/54704 A1 | 9/2000 |

* cited by examiner

Primary Examiner—Gregory Vidovich
Assistant Examiner—Jermie E. Cozart

(57) ABSTRACT

A method of manufacturing medical devices of a size sufficiently small to be passed through the vasculature of the body, and more particularly through the small vessels of the brain. The method includes the steps of laser cutting a pattern of apertures in the surface of a tubular workpiece, radially compressing the tubular workpiece to reduce the outer dimensions of the workpiece and heat setting the reduced diameter workpiece to form the very small medical device.

9 Claims, 2 Drawing Sheets

METHOD OF MANUFACTURING SMALL PROFILE MEDICAL DEVICES

BACKGROUND OF THE INVENTION

1. Field of the Invention

The present invention relates to a method of manufacturing a small medical devices from hollow workpieces, and more particularly, relates to a method which may be used to manufacture very small, thin-walled, tubular devices such as embolic coil retrievable devices, or stents.

2. Description of the Prior Art

For many years, small medical devices such as dilatation balloons, stents and vasculature occlusion devices have been placed within the vasculature of the body. One such occlusion device used for occlusion of a vessel or of an aneurysm is an embolic coil. More recently, such devices have been manufactured to be of a size sufficiently small such that these devices may be placed into vessels of the human brain.

Examples of such catheter-based medical devices are disclosed in U.S. Pat. No. 5,108,407, entitled "A Method And Apparatus For Placement Of An Embolic Coil;" U.S. Pat. No. 5,122,136, entitled, "Endovascular Electrically Detachable Guidewire Tip For The Electroformation Of Thrombus In Arteries, Veins, Aneurysms, Vasculature Malformations And Arteriovenous Fistulas." These patents disclose embolic coils and devices for placing the coils at selected positions within a vessel of the brain in order to treat aneurysms, or alternatively, to occlude a blood vessel at a particular location.

Stents have also been placed within vessels of the brain. Such devices may take the form of a helically wound wire or tubular like structures formed by removing patterns of material from the walls of a tube in order to define a generally skeletal structure.

Stents are generally formed of materials that maintain their shape under the pulsatile flow conditions encounters when placed within a vessel of the body. Some materials that have been used to make such stents include metals and alloys, such as for example, stainless steel, tantalum, tunston and nitinol.

In the event a decision is made to remove an embolic coil from a vessel a coil retrieval system is inserted into the vasculature, such as a vessel of the brain, in order to retrieve the embolic device. Generally, the coil retrieval system includes a grasping mechanism mounted on the distal tip of a catheter. The grasping mechanism is used to grasp and contain a coil and is generally formed for the use of two or more jaws which are normally biased outwardly. When this grasping mechanism is placed within a positioning catheter the jaws are urged to a closed position in order to permit the retrieval device to be passed through the vasculature of the body to a position adjacent to the coil. Once the distal end of the positioning catheter is placed adjacent to the coil, the grasping mechanism is moved out of the catheter to thereby cause the arms to open for subsequent capture of the coil. The gripping mechanism is then withdrawn into the catheter thereby causing the arms to latch, or grip, the coil for removal from the vessel.

In the manufacture of certain small medical devices, such as stents, lathes have been used to support a tubular workpiece used to form the stent during the cutting process. Typically a piece of tubing is supported between a drive mechanism and a tail stock support in lathe. A laser cutting beam is positioned above the tubing to cut a preselected pattern by moving the beam relative to the tubing along the length of the stent. The tubing is then rotated, as necessary, in order to cut along the entire circumference of the tubular workpiece. After the pattern is completely cut, the tubing is cut first at the tail stock end and then at the drive end to form a finished stent. This laser cutting technique for manufacturing stents has proven to be very satisfactory for the manufacture of such medical devices of a size to be used in coronary arteries of the body. Such stents generally have an outer diameter of on the order of about 0.041 inches. Examples of such a laser cutting apparatus and method of use are illustrated in U.S. Pat. No. 5,852,277, entitled, "Laser Cutting Tool For Cutting Elongated Hollow Workpieces" and U.S. Pat. No. 6,114,653, entitled, "Method Of Cutting Hollow Workpieces With A Laser."

On the other hand, it has been found that in order to manufacture very small medical devices, such as stents or embolic coil retrieval devices, to be used in the very small, vessels of the brain, known laser cutting techniques have several limitations. For example, to manufacture such small devices, it is necessary that the diameter of the initial tubular workpiece be very small. At this small initial tube diameter, when metal is cut from the wall of the tube, some molten residual metal is forced to the interior of the tube, thereby lodging in the inner lumen of the workpiece. It is extremely difficult to remove such material, or debris, from the inside of the tube. In addition, it is very difficult to cut through one of the walls of such a small tube by use of laser cutting without damaging the opposite wall of the tube.

SUMMARY OF THE INVENTION

This invention relates to a method for cutting a pattern along the length of a thin-walled, hollow workpiece, to form a small profile medical device, such as a small stent or embolic coil retrieval device, which is more reliable and is more exact.

In accordance with one aspect of the present invention, there is provided a method of manufacturing small profile medical devices from generally tubular workpieces comprising the steps of generating a laser beam to be used for cutting, cutting through the surface of a tubular workpiece of a first predetermined diameter with said laser beam to form a pattern cut along the circumference of the workpiece, radially compressing the tubular workpiece so as to reduce the diameter of the workpiece to a second diameter smaller than the first predetermined diameter, and heating the tubular workpiece to a temperature sufficient to heat set the tubular workpiece to thereby fix the diameter of the tubular workpiece at the smaller diameter.

In accordance with another aspect of the present invention, the cutting step forms a pattern cut which results in the removal of multiple diamond-shaped sections from the surface of the tubular workpiece.

In accordance with still another aspect of the present invention, the tubular workpiece is comprised of a nickel-titanium alloy, such as nitinol.

In accordance with still another aspect of the present invention, after being compressed the tubular member is heated to a temperature necessary to heat set nitinol material. In accordance with still another aspect of the present invention, the tubular member after being compressed is heated to about 450 degrees centigrade for about three minutes in order to heat set the workpiece.

In accordance with still another aspect of the present invention, the cutting step is performed in a manner to cause the material removed from the tubular workpiece to be of a configuration to form the workpiece into a tubular skeleton to prior to the workpiece being radially compressed.

The purpose of this invention is to make a small profile medical device which is very difficult to accurately fabricate by laser cutting a small tube. One of the problems associated with cutting a small tube is that since the inside dimension of the tube is so small that when material is removed from the wall, this material is forced inside of the tube thereby clogging the tube. It is extremely difficult, if not impossible to remove this debris from the inside of the tube. This invention relates to laser cutting a larger tube and then "down sizing" the tube through compression and heat setting. The initial tube size may be 0.048 inches and the resulting medical device may have an outside diameter of 0.016 inches.

DESCRIPTION OF A PREFERRED EMBODIMENT

Figure 1:
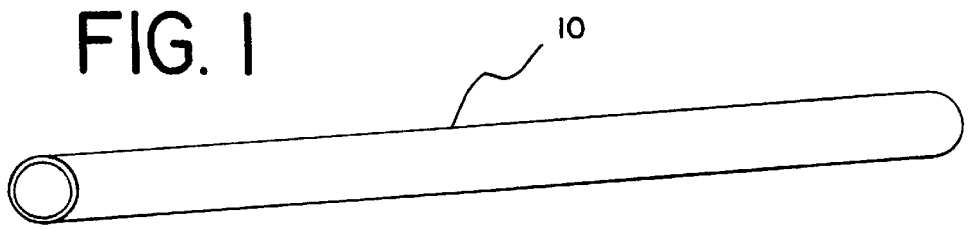
FIG. 1 is a perspective view of a tubular workpiece prior to being processed in accordance with the method of the present invention.
Figure 2:
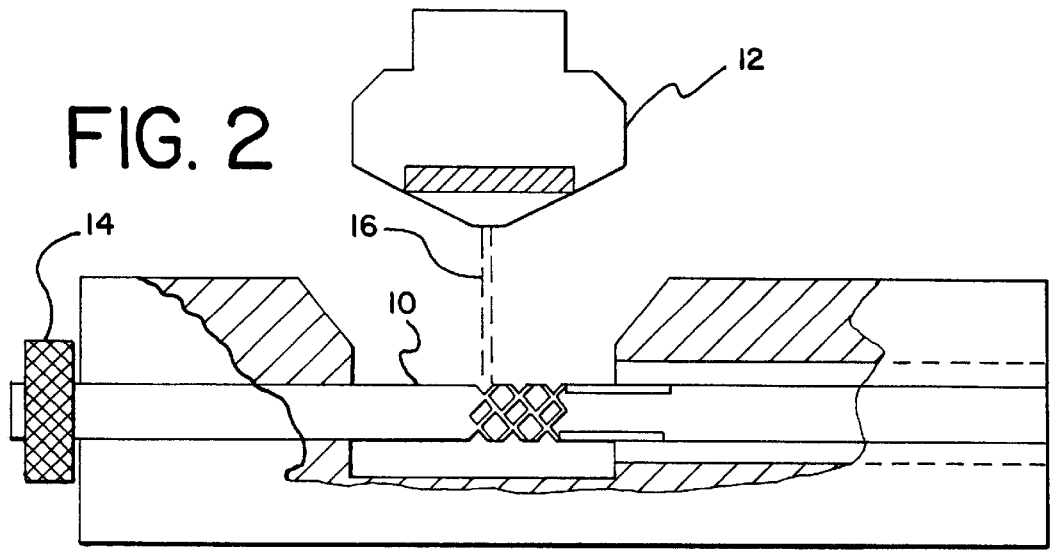
FIG. 2 is a perspective view, partially in section, of an apparatus used to laser cut a tubular workpiece.

FIG. 1 illustrates an elongated metallic tube, preferably formed from a nickel-titanium alloy, such as nitinol, which becomes the tubular workpiece for the present method of fabrication. As illustrated in FIG. 2, the elongated tube 10 is placed into a tube holding collet 14 and is positioned under a laser cutting head 12. The laser cutting head 12 generates a downwardly directed laser beam 16 for cutting apertures, or holes, around the circumference of and along the length of the elongated tube 10. Preferably, the apertures take the form of diamond shapes which configuration aids in a subsequent composition step.

Figure 3:
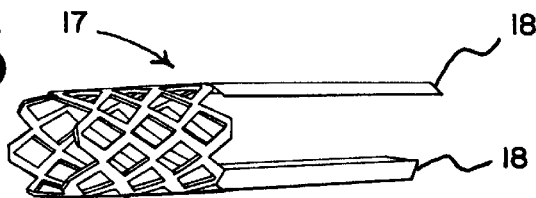
FIG. 3 is a side elevational view of the workpiece after being laser cut with an apparatus as illustrated in FIG. 2.

FIG. 3 illustrates a workpiece 17, in this case the distal gripping portion of an embolic coil retrieval device which has been cut from the elongated tube 10 and which is produced by the cutting method of FIG. 2. The workpiece 17 takes the form of a skeletal section 20 formed by removing diamond shaped pieces from the elongated tube 10 and a pair of actuator arms 18. It should be appreciated, however, that numerous other medical devices such as stents, may also be fabricated using this method of fabrication.

Figure 4:
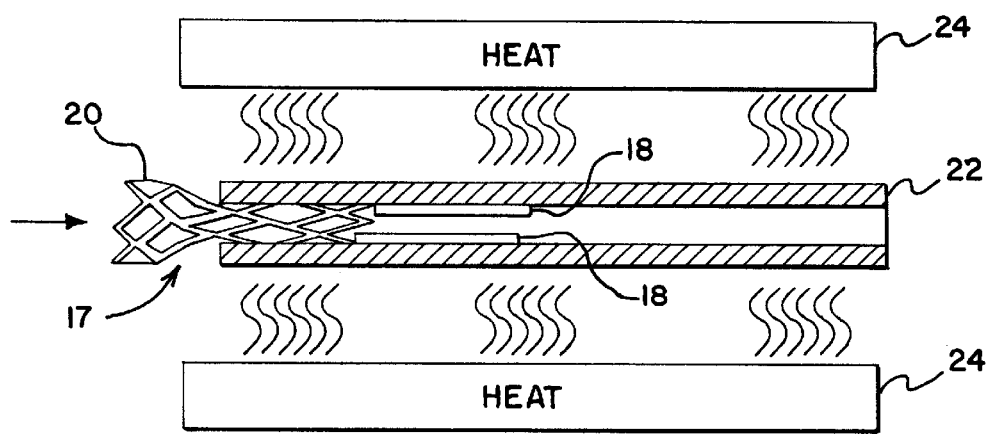
FIG. 4 is a partial, side elevational view which illustrates the method steps of radially compressing the tubular workpiece and subsequently heat setting the workpiece after the compression step is completed.

FIG. 4 illustrates a method of radially compressing the workpiece 17 by inserting the workpiece 17 into a tubular shaping die 22. When the workpiece 17 has been completely moved into the shaping die 22 thereby reducing the diameter of the workpiece 17 from the first larger diameter shown in FIG. 3 to a second smaller diameter. Heat is applied to the workpiece 17 by a heat source 24 which is placed around the circumference of the tubular shaping die 22. The heat source serves to heat the entire assembly to a temperature sufficient to heat set the workpiece 17. In the case of a nitinol material, the heat source 24 heats the entire workpiece 17 to a temperature of approximately 450 degrees centigrade for about 2 to 3 minutes in order to heat set this material.

Figure 4A:
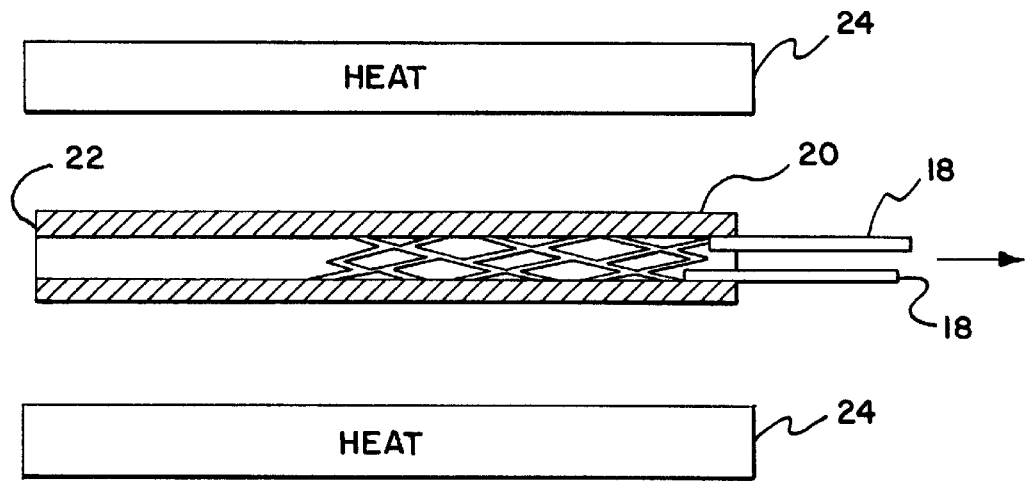
FIG. 4a is a sectional view which illustrates the method of removing the workpiece after compression and heat setting have occurred.

As shown in FIG. 4a, after the completion of the heat set operation, the workpiece 17 is permitted to cool and is removed from the tubular shaping die 22. At this point the workpiece 17 has a diameter which is set by the radial compression and heat set process.

Figure 5:
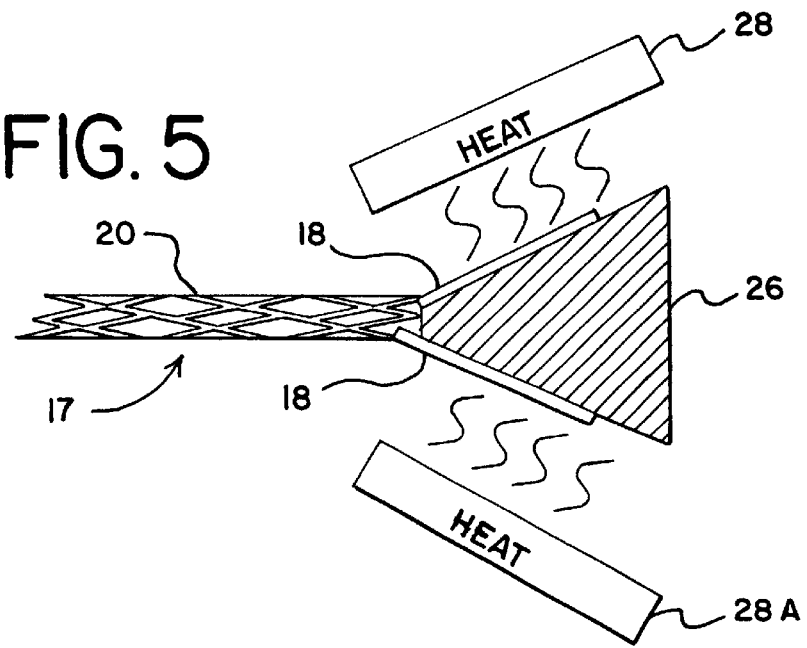
FIG. 5 is a sectional view which illustrates the method step of heat setting the gripping arms of the partially formed embolic coil retrieval device; and, FIG. 6 is a partial side elevational view of the distal gripping portion of an embolic coil retrieval device.

FIG. 5 illustrates the process of forming the actuator arms 18 on an element shaping die 26 by again applying heat sources 28, 28A to heat set the actuator arms 18 in order to cause these arms to be biased into a generally open position. Upon completion of this heat set process, the actuator arms 18 are permitted to cool.

Figure 6:
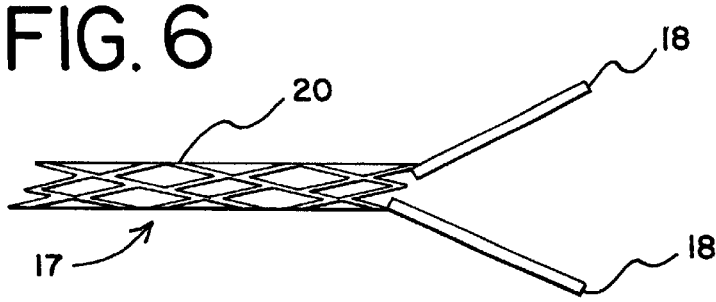

Finally, FIG. 6 illustrates a partially completed distal gripping mechanism of the embolic coil retrieving device. In use, the gripping mechanism is mounted on the distal end of a guidewire and is inserted into a positioning catheter prior to use. Thus it may be appreciated that when the coil retrieving device is placed within a catheter, the actuating arms 18 are biased by the inside lumen of the catheter into a closed, or retracted, position.

Accordingly, with the method of the present invention, it is possible to laser cut an elongated tubular workpiece of a size sufficient to be accurately cut by such laser techniques. Once the workpiece is so cut, it may be forced within a shaping die to reduce the diameter of the workpiece and subsequently heat set to cause the workpiece to remain at the reduced diameter. Once the workpiece has cooled, it may then be removed from the shaping die with the result that the workpiece now forms a very small medical device. With this technique it is possible to laser cut a tube having an outer diameter on the order of about 0.048 inches and produce a medical device having a finished outer diameter of about 0.016 inches.

Various modifications of this invention will become apparent to those skilled in the art. Thus, the scope of the invention is to be limited only by the appended claims.

That which is claimed is:

1. A method of manufacturing a small profile medical device from a generally tubular workpiece comprising the steps of:
   a) generating a laser beam to be used for cutting;
   b) cutting through a surface of the tubular workpiece having a first predetermined outer diameter with said laser beam to form a pattern cut around the circumference of the workpiece;
   c) radially compressing the tubular workpiece so as to reduce the outer diameter of the workpiece to a second outer diameter smaller than the first predetermined diameter; and,
   d) heating the tubular workpiece to a temperature sufficient to heat set the tubular workpiece so that the second outer diameter of the tubular workpiece is fixed to thereby provide a medical device.

2. A method of manufacturing a small profile medical device as defined in claim 1, wherein the surface of the tubular workpiece is cut to form a pattern cut which results in the removal of multiple diamond shaped sections from the surface of the tubular workpiece.

3. A method of manufacturing a small profile medical device as defined in claim 2, wherein the tubular workpiece is comprised of nitinol.

4. A method of manufacturing a small profile medical device as defined in claim 3, wherein the tubular workpiece is heated to a temperature necessary to heat set nitinol material.

5. A method of manufacturing a small profile medical device as defined in claim 4, wherein the tubular workpiece is heated to a temperature of approximately 450 degrees centigrade for approximately three minutes to heat set the workpiece to the second outer diameter.

6. A method of manufacturing a small profile medical device as defined in claim 1, wherein the surface of the tubular workpiece is cut to cause material to be removed from the tubular workpiece to thereby form a generally skeletal configuration.

7. A method of manufacturing a small profile medical device as defined in claim 6, wherein the tubular workpiece is comprised of nitinol.

8. A method of manufacturing a small profile medical device as defined in claim 7, wherein the tubular workpiece is heated to a temperature necessary to heat set nitinol material.

9. A method of manufacturing a small profile medical device as defined in claim 8, wherein the tubular workpiece is heated to a temperature of approximately 450 degrees centigrade for approximately three minutes to heat set the workpiece at the second outer diameter.

* * * * *